(12) United States Patent
Kanakasabhapathi et al.

(10) Patent No.: US 11,005,220 B2
(45) Date of Patent: May 11, 2021

(54) MEDICAL IMAGING DEVICE CONNECTOR ASSEMBLY

(71) Applicant: KONINKLIJKE PHILIPS N.V., Eindhoven (NL)

(72) Inventors: Sujith Kanakasabhapathi, Acton, MA (US); Eugenijus Jagminas, Wakefield, MA (US); Dino Francesco Cuscuna, Reading, MA (US); John Bench Caswell, Manchester, NH (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/630,635

(22) PCT Filed: Jul. 11, 2018

(86) PCT No.: PCT/EP2018/068857
§ 371 (c)(1),
(2) Date: Jan. 13, 2020

(87) PCT Pub. No.: WO2019/025148
PCT Pub. Date: Feb. 7, 2019

(65) Prior Publication Data
US 2020/0169046 A1 May 28, 2020

Related U.S. Application Data

(60) Provisional application No. 62/531,393, filed on Jul. 12, 2017.

(51) Int. Cl.
| | | |
|---|---|---|
| A61B 1/005 | (2006.01) | |
| H01R 13/66 | (2006.01) | |
| A61B 1/00 | (2006.01) | |
| A61B 8/00 | (2006.01) | |
| H01R 12/82 | (2011.01) | |
| H01R 13/502 | (2006.01) | |
| H01R 13/52 | (2006.01) | |
| H01R 13/58 | (2006.01) | |
| H01R 13/7193 | (2011.01) | |

(52) U.S. Cl.
CPC ......... *H01R 13/6658* (2013.01); *A61B 1/005* (2013.01); *A61B 1/00124* (2013.01);
(Continued)

(58) Field of Classification Search
CPC ............ H01R 13/7193; H01R 13/5213; H01R 13/6658; H01R 13/502; H01R 13/5202;
(Continued)

(56) References Cited

U.S. PATENT DOCUMENTS

| 4,846,724 A | 7/1989 | Sasaki et al. |
| 5,678,551 A | 10/1997 | Stevens |
(Continued)

FOREIGN PATENT DOCUMENTS

EP 2478825 A1 7/2012

OTHER PUBLICATIONS

International Search Report and Written Opinion for International Application No. PCT/EP2018/068857, filed Jul. 11, 2018, 20 pages.

*Primary Examiner* — Tho D Ta

(57) ABSTRACT

A medical imaging device connector assembly (400) for connecting a medical imaging device (900) to a terminal of a medical imaging system (10) is provided. The medical imaging device connector assembly includes a first housing (410) including an opening (412) sized and shaped to receive at least one electrical connector (800), a second housing (420), a first internal frame (430) configured to be secured to the first housing, a second internal frame (440) configured to be secured to the second housing, and at least one printed circuit board (610, 620) disposed between the first internal frame and the second internal frame when the first internal frame is secured to the second internal frame.

20 Claims, 15 Drawing Sheets

(52) U.S. Cl.
CPC ........... *A61B 8/4483* (2013.01); *H01R 12/82* (2013.01); *H01R 13/502* (2013.01); *H01R 13/5202* (2013.01); *H01R 13/5205* (2013.01); *H01R 13/5213* (2013.01); *H01R 13/58* (2013.01); *H01R 13/7193* (2013.01); *H01R 2201/12* (2013.01)

(58) Field of Classification Search
CPC ............ H01R 13/5205; H01R 2201/12; H01R 12/82; Y10S 439/909; A61B 1/00124; A61B 1/005
See application file for complete search history.

(56) References Cited

U.S. PATENT DOCUMENTS

| | | | |
|---|---|---|---|
| 6,083,053 A * | 7/2000 | Anderson, Jr. | H01R 24/84 |
| | | | 439/687 |
| 6,117,084 A | 9/2000 | Green et al. | |
| 6,428,330 B1 * | 8/2002 | Poulter | H04L 12/4604 |
| | | | 439/607.23 |
| 6,440,076 B1 | 8/2002 | Sudol et al. | |
| 6,722,897 B1 * | 4/2004 | Wu | H01R 31/06 |
| | | | 439/76.1 |
| 7,458,824 B2 * | 12/2008 | Ogawa | H05K 7/026 |
| | | | 439/76.1 |
| 8,480,433 B2 * | 7/2013 | Huang | B60R 16/0232 |
| | | | 439/620.21 |
| D692,564 S | 10/2013 | Ninomiya et al. | |
| 8,753,280 B2 | 6/2014 | Zhao | |
| 2004/0111029 A1 | 6/2004 | Bates et al. | |
| 2007/0197057 A1 * | 8/2007 | Wu | H01R 31/06 |
| | | | 439/76.1 |
| 2008/0305658 A1 * | 12/2008 | Ko | H01R 13/5808 |
| | | | 439/76.1 |
| 2009/0240146 A1 | 9/2009 | Bockenstedt et al. | |
| 2012/0071021 A1 | 3/2012 | Wu | |

\* cited by examiner

MEDICAL IMAGING DEVICE CONNECTOR ASSEMBLY

RELATED APPLICATIONS

This application is the U.S. National Phase application under 35 U.S.C. § 371 of International Application No. PCT/EP2018/068857, filed on Jul. 11, 2018, which claims the benefit of Provisional Application No. 62/531,393, filed Jul. 12, 2017. These applications are hereby incorporated by reference herein.

TECHNICAL FIELD

The present disclosure relates generally to medical imaging and, in particular, to connector assemblies of a medical imaging device. For example, an ultrasound imaging device connector assembly can include a front housing configured to be secured to a front internal frame and a back housing configured to be secured to a back internal frame.

BACKGROUND

Medical imaging devices are widely used as a diagnostic tool for internally or externally assessing physiology to determine the need for treatment and assessing the effectiveness of the treatment. When in use, the medical imaging device is in contact with tissue and/or fluids of the patient, saline solution, ultrasound gel, and/or other substances which render the imaging device non-sterile. In the case of re-usable devices, upon conclusion of the imaging, the medical imaging device is disinfected with use of enzymatic cleaners and disinfectants before it can be used again. In some instances, the medical imaging device is sterilized within an autoclave. The imaging device, along with a cable and a connector assembly connected thereto, are therefore exposed to a highly humid environment. The electrical connectors and printed circuit boards inside the connector assemblies are especially prone to failure due to ingress of enzymatic cleaners, disinfectants, bodily fluids, saline solutions, ultrasound gel, and/or or to exposure to the humid environment.

While the existing connector assemblies of medical imaging devices generally attempt to prevent ingress of fluids during operation and sterilization, they are not satisfactory in all aspects. There is a need for a medical imaging device with a connector assembly that can better protect electrical circuitry and connectors therein from fluid ingress.

SUMMARY

Embodiments of the present disclosure provide a medical imaging device connector assembly for connecting a medical imaging device to a terminal of a medical imaging system. The medical imaging device connector assembly includes a front housing, a back housing, a front internal frame and a back internal frame, with the front housing having an opening to receive at least one electrical connector. When assembled, the front housing is secured to the front internal frame, the back housing is secured to the back internal frame, and the front internal frame is secured to the back internal frame. Inside the medical imaging device connector assembly is at least one printed circuit board disposed between the front internal frame and the back internal frame along a planar direction of the at least one printed circuit board. To prevent ingress of moisture, bodily fluids, saline solutions, ultrasound gel, enzymatic cleaners or disinfectants into the medical imaging device connector assembly and damages to the at least one printed circuit board, the medical imaging device connector assembly includes two gaskets. One gasket is disposed between the front housing and the front internal frame and the other is disposed between the front housing and the back housing. In some instances, the medical imaging device connector assembly may further include a conical cable housing. To accommodate the conical cable housing, each of the front and back housings has a semi-circular edge recess and the gasket disposed between the front and back housings has a circular-shaped member. In some examples, the at least one electrical connector is at least one zero insertion force (ZIF) connector.

In one embodiment, a medical imaging device connector assembly for connecting a medical imaging device to a terminal of a medical imaging system is provided. The medical imaging device connector assembly includes a first housing including an opening sized and shaped to receive at least one electrical connector, a second housing, a first internal frame configured to be secured to the first housing, a second internal frame configured to be secured to the second housing, and at least one printed circuit board disposed between the first internal frame and the second internal frame when the first internal frame is secured to the second internal frame.

In some embodiments, the second internal frame of the medical imaging device connector assembly includes a recess sized and shaped to receive a portion of a ferrite tube. In some embodiments, the second housing of the medical imaging device connector assembly includes a recess sized and shaped to receive a portion of the ferrite tube. In some embodiments, the at least one printed circuit board includes two printed circuit boards and a portion of the two printed circuit boards are inserted into slots disposed in the second internal frame. In some embodiments, the medical imaging device connector assembly further includes a gasket. The first housing includes a first groove configured to receive a portion of the gasket and the second housing includes a second groove configured to receive a portion of the gasket. Further, the gasket is disposed between the first groove and the second groove when the first housing is secured to the first internal frame and the second housing is secured to the second internal frame. In some embodiments, the gasket disposed between the first and second grooves is referred to as a first gasket and the medical imaging device connector assembly further includes a second gasket. The first internal frame includes a third groove configured to receive a portion of the second gasket. In addition, when the first housing is secured to the first internal frame, the second gasket is disposed between the first housing and the third groove. In some embodiments, the at least one electrical connector of the medical imaging device connector assembly is at least one zero insertion force (ZIF) connector. In some embodiments, the at least one electrical connector is at least one female ZIF connector configured to be electrically connected to at least one male ZIF connector. In some embodiments, the terminal of the medical imaging system includes the at least one male ZIF connector.

Embodiments of the present disclosure also provides a medical imaging device that includes an imaging assembly at a distal portion of a flexible elongate member, and a connector assembly at a proximal portion of the flexible elongate member, wherein the connector assembly is configured to connect the medical imaging device to a terminal of a medical imaging system. The connector assembly includes a conical cable housing, a front housing, and a back housing. The conical cable housing has a proximal end and a distal end. The proximal end has a first outer diameter and the distal end has a second outer diameter smaller than the first outer diameter. The front housing includes an opening sized and shaped to receive at least one electrical connector, and a semi-circular edge recess configured to receive a portion of a circumference of the proximal end of the conical cable housing. The back housing includes a semi-circular edge recess configured to couple to a portion of the circumference of the proximal end of the conical cable housing.

In some embodiment, the connector assembly of the medical imaging device further includes a front internal frame configured to be secured to the front housing, a back internal frame configured to be secured to the back housing, and at least one printed circuit board securely clamped along a planar direction thereof between the front internal frame and the back internal frame when the front internal frame is secured to the back internal frame. In some embodiments, the back internal frame includes a recess sized and shaped to receive a portion of a ferrite tube. In some embodiments, the back housing of the medical imaging device includes a recess sized and shaped to receive a portion of the ferrite tube. In some embodiments, the at least one printed circuit board includes two printed circuit boards and a portion of the two printed circuit boards are inserted into slots disposed in the back internal frame. In some embodiments, the connector assembly further comprises a gasket. The front housing includes a first groove configured to receive a portion of the gasket and the first groove includes a first curved groove positioned on the semi-circular edge recess. The back housing includes a second groove configured to receive a portion of the gasket and the second groove includes a second curved groove positioned on the semi-circular edge recess. When the front housing is secured to the front internal frame and the back housing is secured to the back internal frame, the gasket is disposed between the first groove and the second groove and between the first and second curved grooves and the circumference of the proximal end of the conical cable housing. In some embodiments, the gasket includes a rectangular-shaped member extending along a first plane and a circular-shaped member extending along a second plane. In some embodiments, the first plane has a first normal direction and the second plane has a second normal direction perpendicular to the first normal direction. In some embodiments, the circumference of the proximal end of the conical cable housing includes a third groove configured to receive a portion of the gasket. In some embodiments, the gasket disposed between the first and second grooves is referred to as a first gasket and the connector assembly further includes a second gasket. The front internal frame includes a third groove configured to receive a portion of the second gasket. When the front housing is secured to the front internal frame, the second gasket is disposed between the front housing and the third groove. In some embodiments, the at least one electrical connector is at least one female zero insertion force (ZIF) connector configured to be electrically connected to at least one male ZIF connector.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
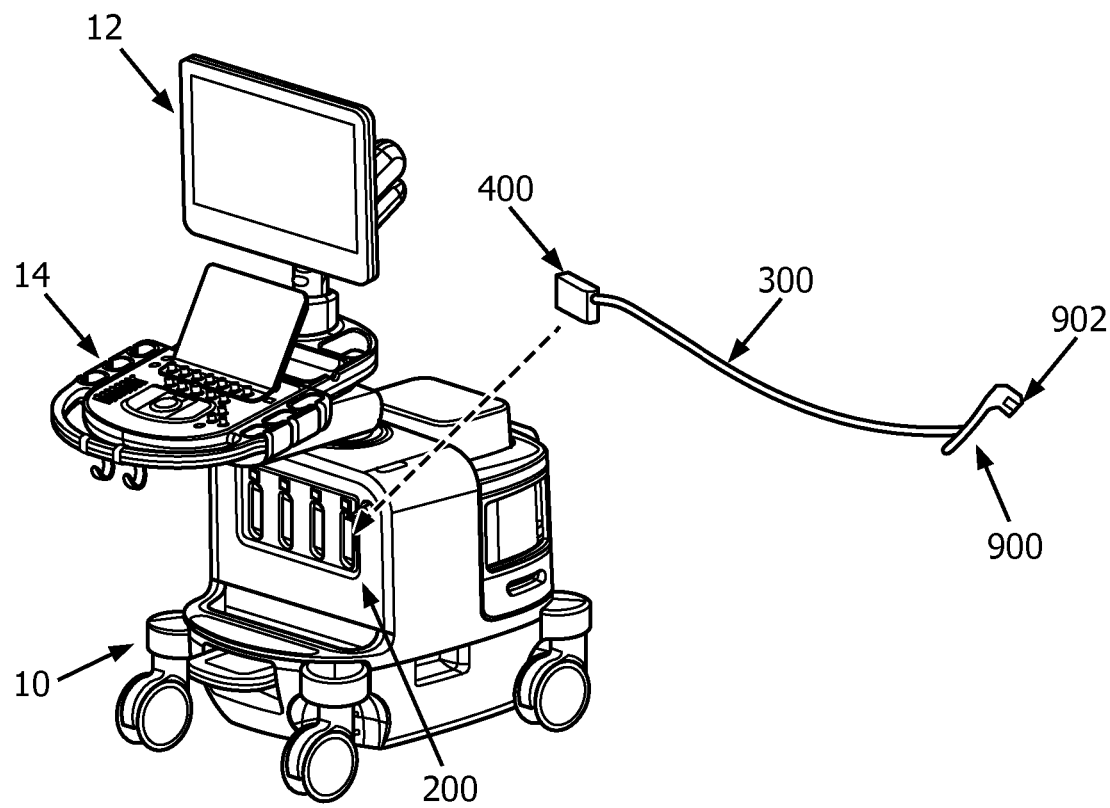
FIG. 1 is a diagrammatic perspective view of a medical imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic perspective view of a medical imaging system 10, according to aspects of the present disclosure. A medical imaging device 900 is connected to a cable 300 coupled to a connector assembly 400. In various embodiments, the medical imaging device 900 can be an ultrasound imaging device, a transesophageal echocardiography (TEE) probe, an endoscope, and/or other suitable devices. A distal portion of the medical imaging device 900 includes an imaging assembly 902. For example, the imaging assembly 902 can include a probe and one or more imaging elements. For example, the imaging elements can be ultrasound transducers, and the imaging assembly 902 can include one or more ultrasound transducer arrays. A proximal portion of the medical imaging device 900 includes the connector assembly 400. The cable 300 extends between the imaging assembly 902 and the connector assembly 400. In some instances, the cable 300 can be referenced as a flexible elongate member.

In some embodiments, the medical imaging device 900 is sized and shaped for positioning within the body of the patient, such as within the esophagus, heart, blood vessel, and/or other body lumen or cavity of the patient. In some embodiments, the medical imaging device 900s is sized and shaped to be positioned on the outside of the body, such as with the imaging assembly 902 in contact with the skin of the patient. The shape of the medical imaging device 900 shown in FIG. 1 is only for illustration purposes and does not in any way limit the shape of the medical imaging device according to aspects of the present disclosure.

In operation, the imaging assembly 902 can obtain imaging data associated with the body of the patient. Electrical signals representative of the imaging data can be transmitted from the imaging assembly 902 to the connector assembly 400 along one or more electrical conductors of the cable 300. The connector assembly 400 can be in mechanical and/or electrical communication with the medical imaging system 10, such that the electrical signals are transmitted from connector assembly 400 to the medical imaging system 10. The system 10 includes one or more processors and/or memory forming a processing circuit that can process the electrical signals and output a graphical representation of the imaging data on a display device 12. The one or more electrical conductors of the cable 300 and/or the connector assembly 400 facilitate communication between the medical imaging system 10 and the medical imaging device 900. For example, a user of the system 10 can control imaging using the medical imaging device 900 via a control interface 14 of the system 10. Electrical signals representative of commands from the system 10 can be transmitted to the medical imaging device 900 via the connector assembly 400 and/or the one or more conductors of the cable 300.

The connector assembly 400 is configured to be insertable into a slot 200 on the medical imaging system 10. Generally, the connector assembly 400 and the slot 200 can include any suitable connections that are configured to mechanically and/or electrically couple to one another. In some embodiments, the connector assembly 400 houses one or more male or female zero insertion force (ZIF) connectors. In such embodiments, the slot 200 includes corresponding female or male ZIF connectors. That way, when the connector assembly 400 is inserted into the slot 200, the male/female connectors in the connector assembly 400 are electrically connected to the female/male connectors in the slot 200.

Figure 2:
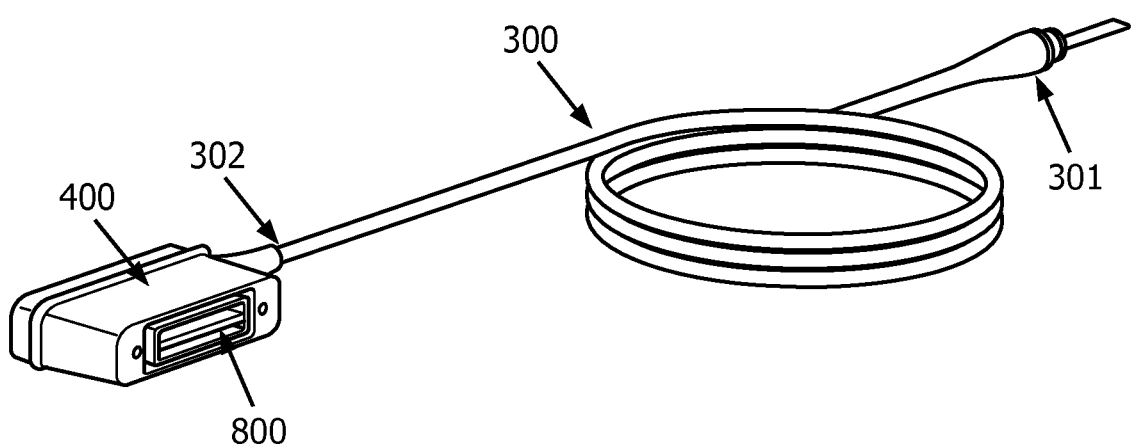
FIG. 2 is a diagrammatic perspective view of a connector assembly and a cable, according to aspects of the present disclosure.

FIG. 2 is a diagrammatic perspective view of a connector assembly 400 and a cable 300, according to aspects of the present disclosure. The cable 300 has a distal end 301 that is connected to the imaging assembly 902 (FIG. 1) and a proximal end 302 that is connected to the connector assembly 400. The cable 300 can include one or more electrical conductors and a conduit surrounding electrical conductors. In some embodiments, the connector assembly 400 includes one or more electrical connectors 800. In the embodiment shown in FIG. 2, the one or more electrical connectors 800 are two female ZIF connectors. In other embodiments, electrical connectors 800 can be male ZIF connectors or any suitable type of male or female electrical connector. In some other embodiments, electrical connectors 800 can include other type of connectors, such as low insertion force (LIF) connectors, flat flexible connectors (FFC), ribbon cable connectors, and serial advanced technology attachment (SATA) connectors.

Figure 3:
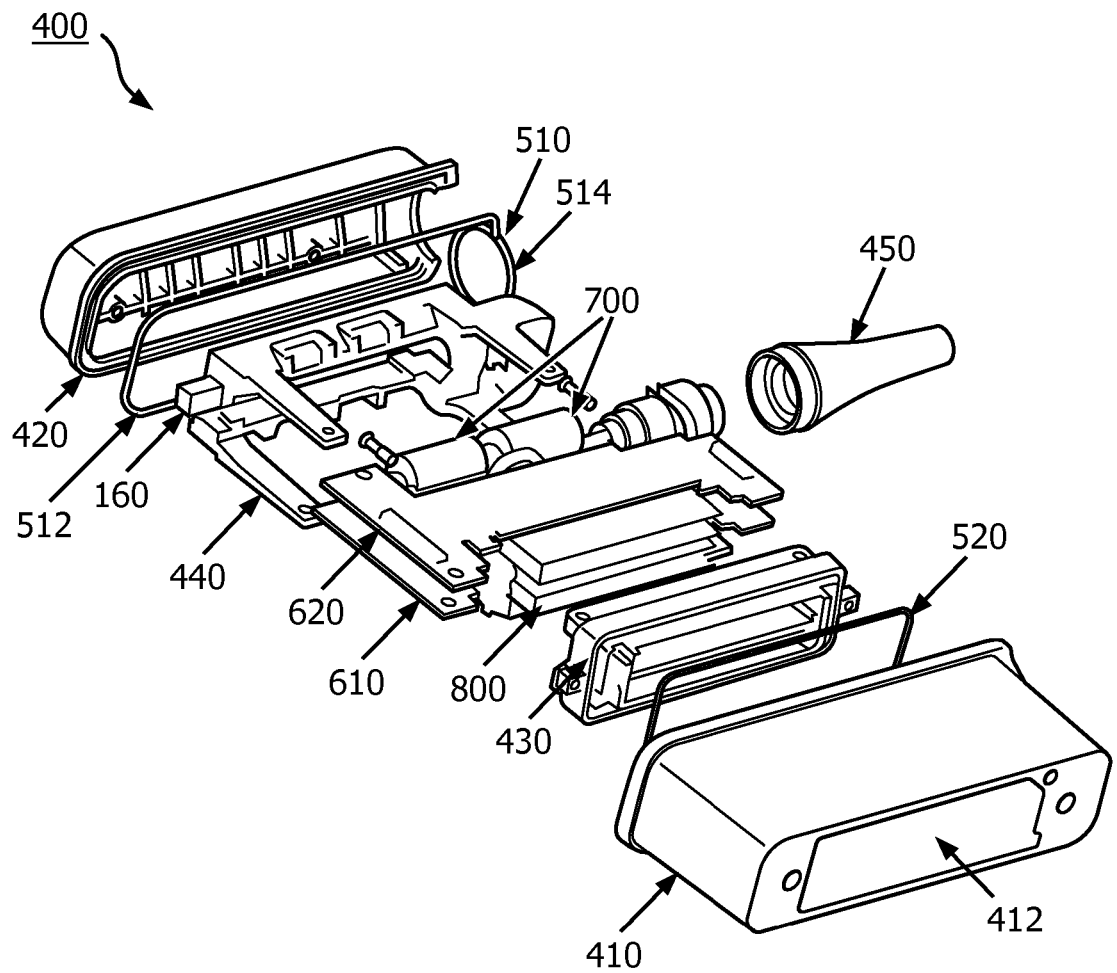
FIG. 3 is a diagrammatic exploded view of a connector assembly, according to aspects of the present disclosure.

FIG. 3 is a diagrammatic exploded view of the connector assembly 400, according to aspects of the present disclosure. In some embodiments, the connector assembly 400 includes a housing 410, a housing 420, an internal frame 430, and an internal frame 440. The exterior of the body of the connector assembly 400 can be formed when the housing 410 and the housing 420 are directly and/or indirectly coupled to one another. The internal frame 430 and the internal frame 440 provide internal structure of the body of the connector assembly 400. In some instances, the housing 410 can be referenced as a front housing, and the internal frame 430 can be referenced as a front internal frame. The housing 420 can be referenced as a back housing, and the internal frame 430 can be referenced as a back internal frame. In the illustrated embodiment, the front housing 410 is larger than the back housing 420. In other embodiments, the back housing 420 is larger than the front housing 410 and/or the housings 410, 420 are similarly sized. The front housing 410 has an opening 412, which provides access to one or more electrical connectors 800. In some instances, the front and back housings 410 and 420 are formed of a metal or a metal alloy to shield off electromagnetic interferences.

In some embodiments, the front and back internal frames 430 and 440 are secured to one another by a plurality of screws. In some instances, the front housing 410 is coupled to the front internal frame 430 by a plurality of screws, and the back housing 420 is coupled to the back internal frame 440 also by a plurality of screws. The front housing 410 and the back housing 420 may be indirectly coupled to one another by being secured to the front and back internal frames 430 and 440, respectively. In addition, in some embodiments as shown in FIG. 3, the internal frame 430 is sized and shaped to house the one or more electrical connectors 800 and is sometimes referred to as a connector housing.

In some embodiments, the connector assembly 400 includes one or more printed circuit boards (PCBs). The PCBs can include one or more electronic components that provide signal conditioning and/or processing for the electrical signals representative of the imaging data obtained by the imaging assembly 902 (FIG. 1). In some instances, there are two printed circuit boards (PCBs) inside the connector assembly 400. As shown in FIG. 3, connector assembly 400 includes a PCB 610 and a PCB 620. The PCBs 610 and 620 are disposed between the front internal frame 430 and the back internal frame 440 when the front internal frame 430 and the back internal frame 440 are secured to one another. In some instances, the PCBs 610 and 620 are planar and extend along two planes parallel to one another. It is noted that in these instances, the PCBs 610 and 620 are not secured along normal directions to the two planes but along the planar directions of them. In some embodiments, the PCBs 610 and 620 include one or more cut-out sections such that when they are arranged side-by-side as shown in FIG. 3, the cut-out sections form space to accommodate one or more ferrite tubes 700. In some embodiments, the ferrite tubes 700 are formed of ferric oxide containing ceramic materials and are used to eliminate radio frequency interference associated with the electrical signals.

In some embodiments, the connector assembly 400 includes one or more gaskets. As shown in FIG. 3, a gasket 510 is disposed between the front housing 410 and back housing 420 when the front housing 410 is secured to the front internal frame 430, the back housing 420 is secured to back internal frame 440, and the front internal frame 430 is secured to the back internal frame 440. Put differently, the gasket 510 is disposed between the front and back housings 410 and 420 when they are indirectly secured to one another by be respectively secured to the front and back internal frames 430 and 440. A gasket 520 is disposed between the front internal frame 430 and an internal surface of the front housing 410 when the front housing 410 is secured to the front internal frame 430. The gaskets 510 and 520 serve as bather of humidity, disinfectants, and enzymatic cleaners and protect the PCBs 610 and 620 from being damaged by ingress of liquids. In some embodiments, the connector assembly 400 includes a conical cable housing 450. The conical cable housing 450 can serve as a cable strain relief to reduce mechanical stress on the cable 300. In some instances, gaskets 510 and 520 are made using stamping or die cutting process out of commercially available elastic sealing materials. In some instances, metal particles are incorporated into gaskets 510 and 520 to shield the connector assembly 400 from electromagnetic interferences.

Figure 4:
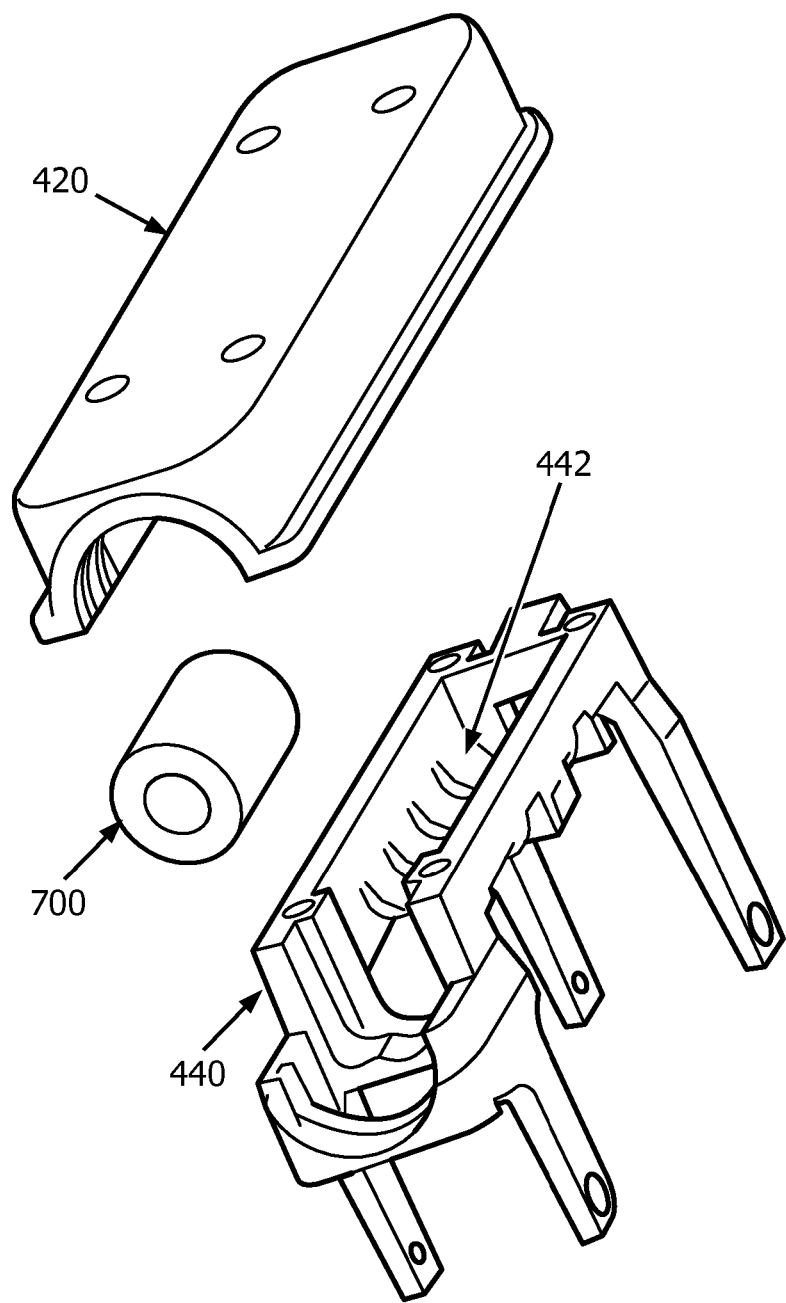
FIG. 4 is a diagrammatic perspective view of a back housing and a back internal frame, according to aspects of the present disclosure.
Figure 5:
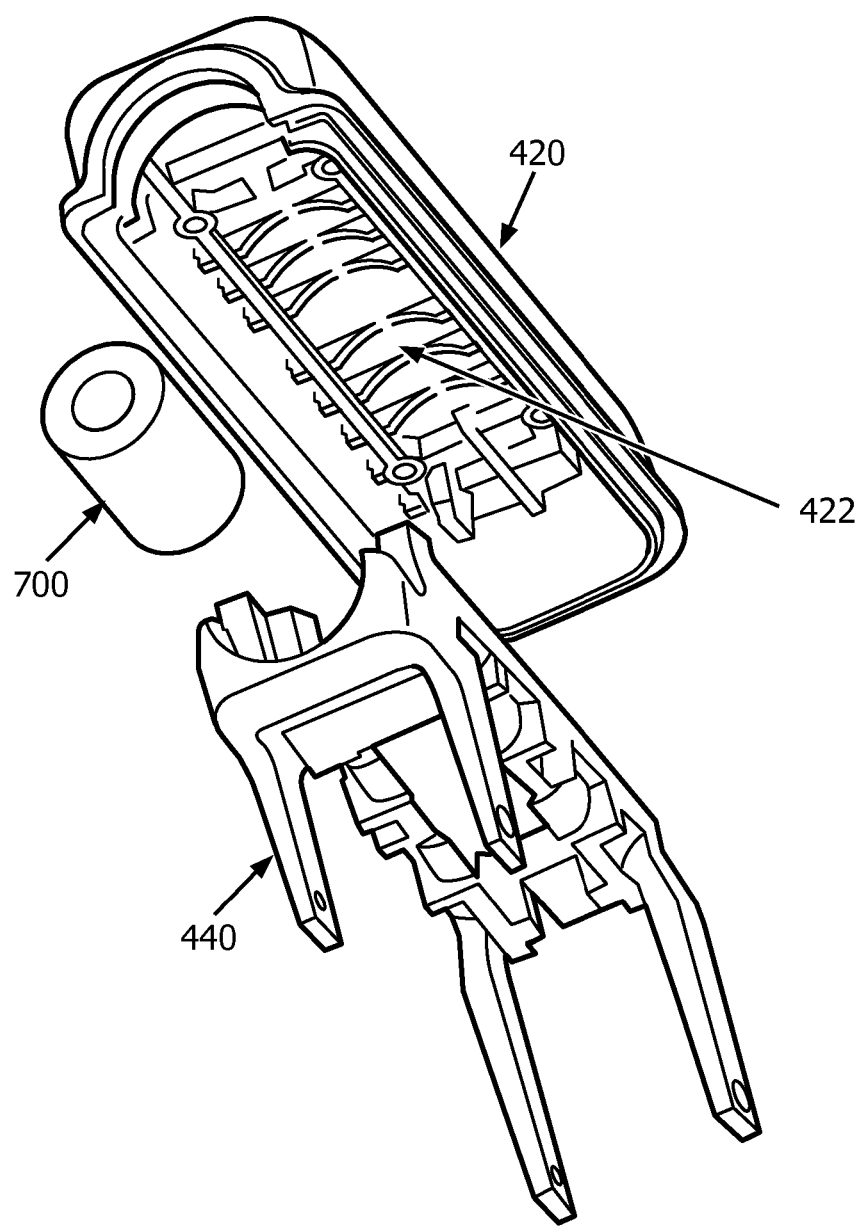
FIG. 5 is another diagrammatic perspective view of a back housing and a back internal frame, according to aspects of the present disclosure.

FIGS. 4 and 5 are diagrammatic perspective views of the back housing 420 and the back internal frame 440, according to aspects of the present disclosure. FIG. 4 can be described as illustrating a downward facing view, while FIG. 5 illustrates an upward facing view of the same components of FIG. 4. As shown in FIG. 4, the back internal frame 440 includes a recess 442. The recess 442 is sized and shaped to receive a portion of one or more ferrite tubes 700. While only one ferrite tube 700 is illustrated in FIGS. 4 and 5, it is understood that the connector assembly 400 can include two or more ferrite tubes 700. As shown in FIG. 5, the back housing 420 includes a recess 422. The recess 422 is sized and shaped to receive a portion of one or more ferrite tubes 700. In some embodiments, the one or more ferrite tubes 700 are cylindrical in shape, with one half of the cylindrical shape being accommodated in the recess 422 and the other half of the cylindrical shape being accommodated in the recess 442. As shown in FIG. 4, with the recess 442 retaining a portion of the one or more ferrite tubes 700, the back internal frame 440 serves as a mounting bracket for the one or more ferrite tubes 700.

Figure 6A:
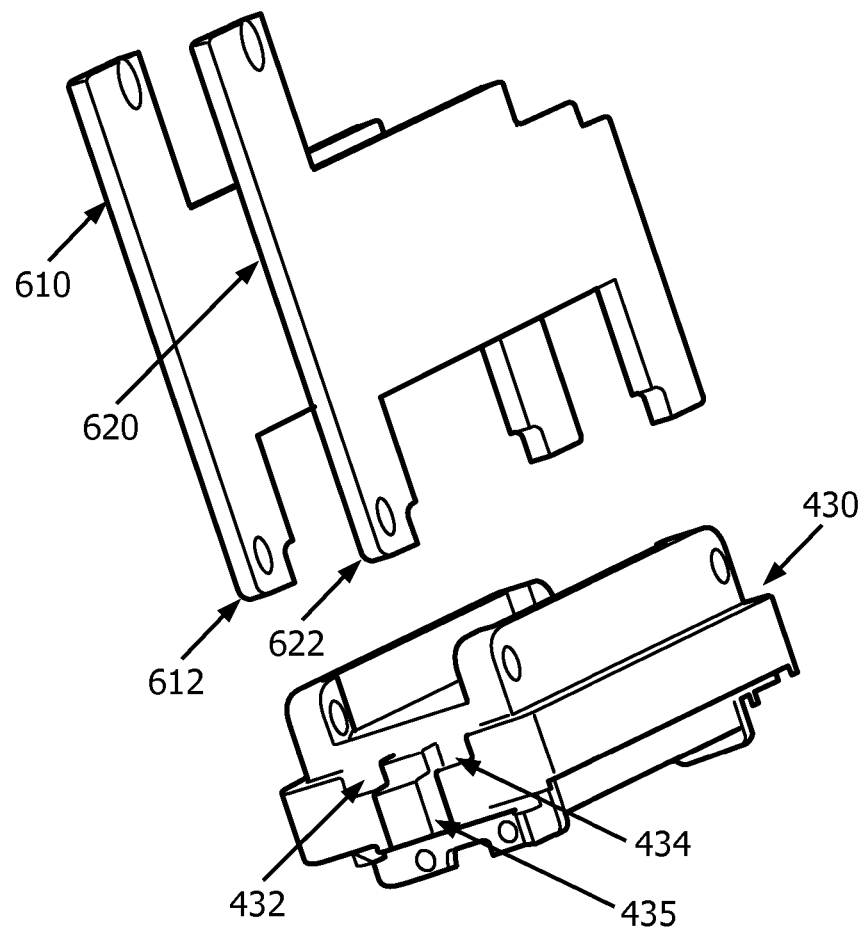
FIG. 6A is a diagrammatic perspective view of a front internal frame and printed circuit boards, according to aspects of the present disclosure.
Figure 6B:
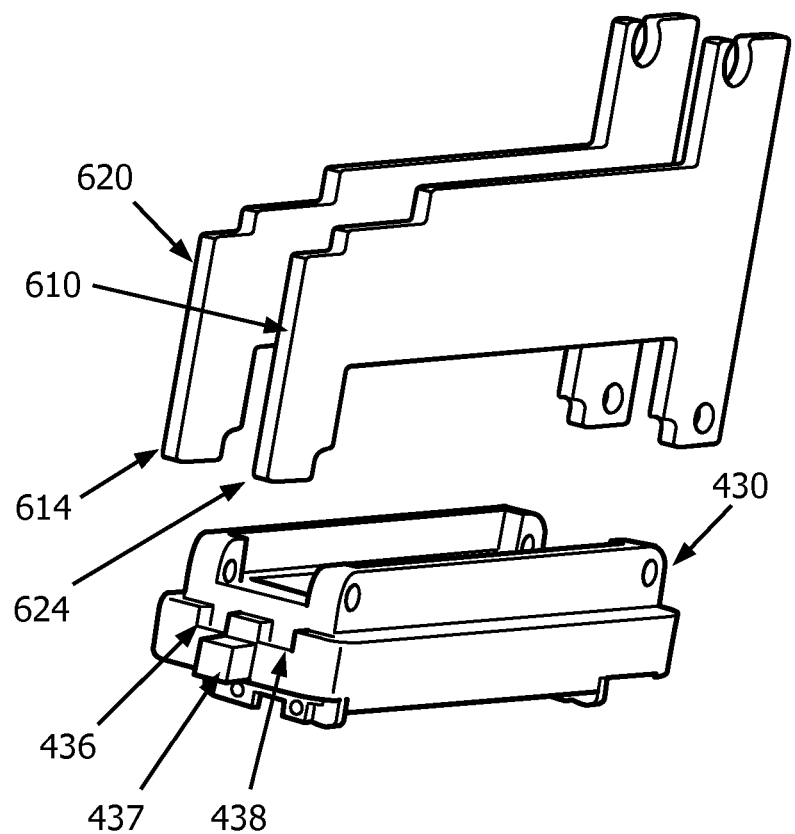
FIG. 6B is another diagrammatic perspective view of a front internal frame and printed circuit boards, according to aspects of the present disclosure.

FIGS. 6A and 6B are diagrammatic perspective views of the front internal frame 430 and the first and second PCBs 610 and 620, according to aspects of the present disclosure. FIGS. 6A and 6B illustrates views that are 180° from one another. For example, FIG. 6A can be a top or bottom view, and FIG. 6B can be a bottom or top view of the same components. As described above, in some embodiments, the connector assembly 400 includes the first PCB 610 and the second PCB 620. When the first and second PCBs 610 and 620 are disposed between the front internal frame 430 and the back internal frame 440, portions 612, 622 on respective distal ends of the first and second PCBs 610 and 620 (away from the distal end 302 of the cable 300) are inserted into slots 432 and 434. In that regard, the slots 432 and 434 and the portions 612, 622 are sized and shaped to engage with one another when the PCBs 610, 620 are in contact with the front internal frame 430. In some embodiments, as shown in FIG. 6B, portions 614, 624 on respective proximal ends of the first and second PCBs 610 and 620 (closer to the distal end 302 of the cable 300) are inserted into slots 436 and 438. In that regard, the slots 436 and 438 and the portions 614, 624 are sized and shaped to engage with one another when the PCBs 610, 620 are in contact with the front internal frame 430. Insertion of portions of the first and second PCBs 610 and 620 into slots 432, 434, 436, and 438 prevents the first and second PCBs 610 and 620 from movement relative to the front internal frame 430.

As shown in FIGS. 6A and 6B, in some instances, the front internal frame 430 also includes a protrusion 435 and a protrusion 437. The pair of protrusions 435 and 437 serve as spacers to maintain a distance between the PCBs 610 and 620. The number of protrusions/spacers can vary, depending on the number of PCBs housed in the connector assembly 400. In instances where there are more than two substantially parallel PCBs, the front internal frame 430 may include more than a pair of protrusions. For example, if three parallel PCBs are desired, the front internal frame 430 may include two pairs of protrusions.

Figure 7:
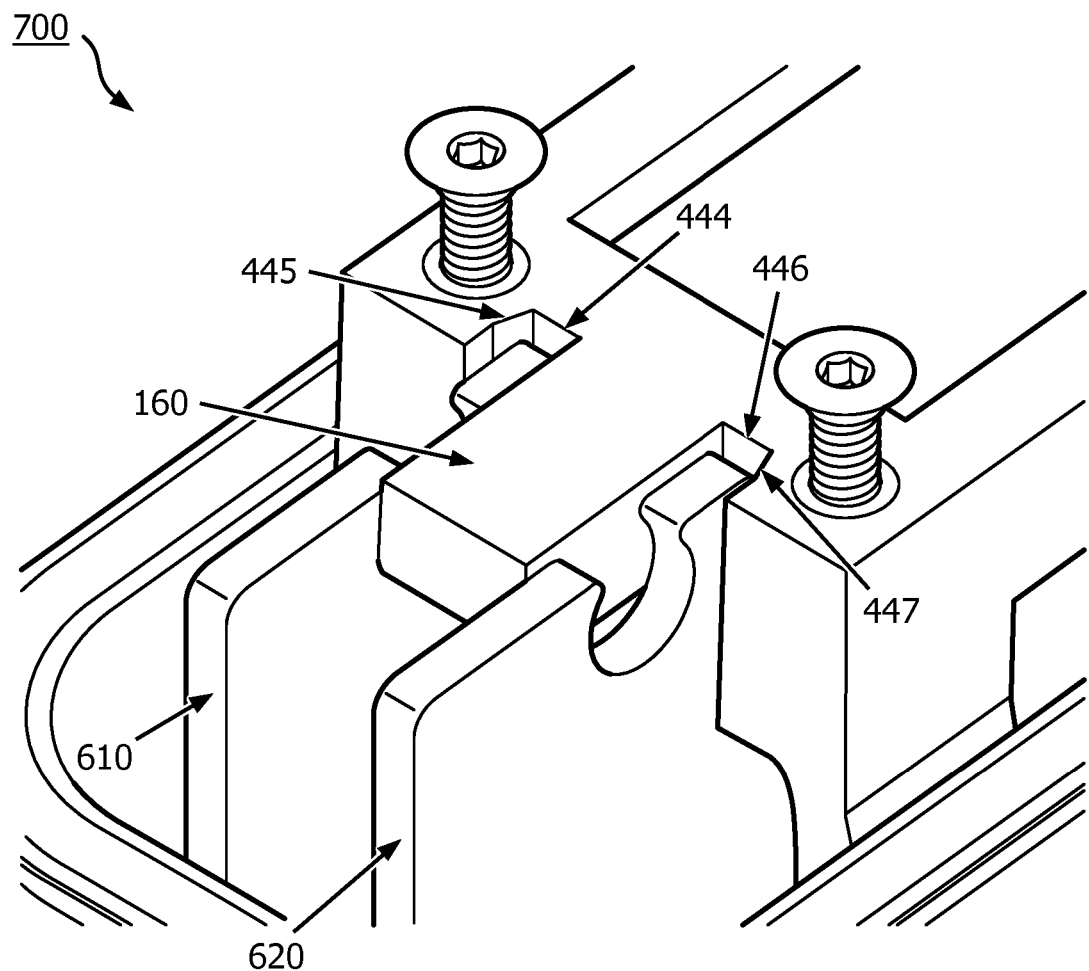
FIG. 7 is a diagrammatic perspective view of a back internal frame and printed circuit boards, according to aspects of the present disclosure.

Shown in FIG. 7 is a diagrammatic perspective view of the back internal frame 440 and the first and second PCBs 610 and 620, according to aspects of the present disclosure. In some embodiments, the back internal frame 440 includes slots 444 and 446. Slots 444 and 446 are sized and shaped to receive a portion of the first and second PCBs 610 and 620. In some instances, each of the slots 444 and 446 has at least one chamfered surface 445 or 447. In some embodiments, the chamfered surfaces 445 and 447 are mirror images of one another. The angles of the chamfered surfaces 445, 447 can be between 1° and 60° in some instances, including values such as 15°, 20°, 30°, 45°, and/or other suitable values. As the portion of the first and second PCBs 610 and 620 is pushed into the back internal frame 440 towards where ferrite tube 700 is positioned, the chamfered surfaces 445 and 447 redirect the applied forces and push the portion of the PCBs 610 and 620 against a protrusion 160 of the back internal frame 440. In this manner, the PCBs 610 and 620 can be secured within the back internal frame 440. The chamfered surfaces 445 and 447 allow easy yet precise assembly of the first and second PCBs 610, 620 and the back internal frame 440. Similar to protrusions 435 and 437 of the front internal frame 430, protrusion 160 of the back internal frame 440 also serves as a spacer to maintain a distance between the first and second PCBs 610 and 620. The number of protrusions of the back internal frame 440 likewise depends on the number of PCBs housed in the connector assembly 400. For example, if the three parallel PCBs are desired to be housed in the connector assembly 400, the back internal frame 440 may include more than protrusions.

Figure 8A:
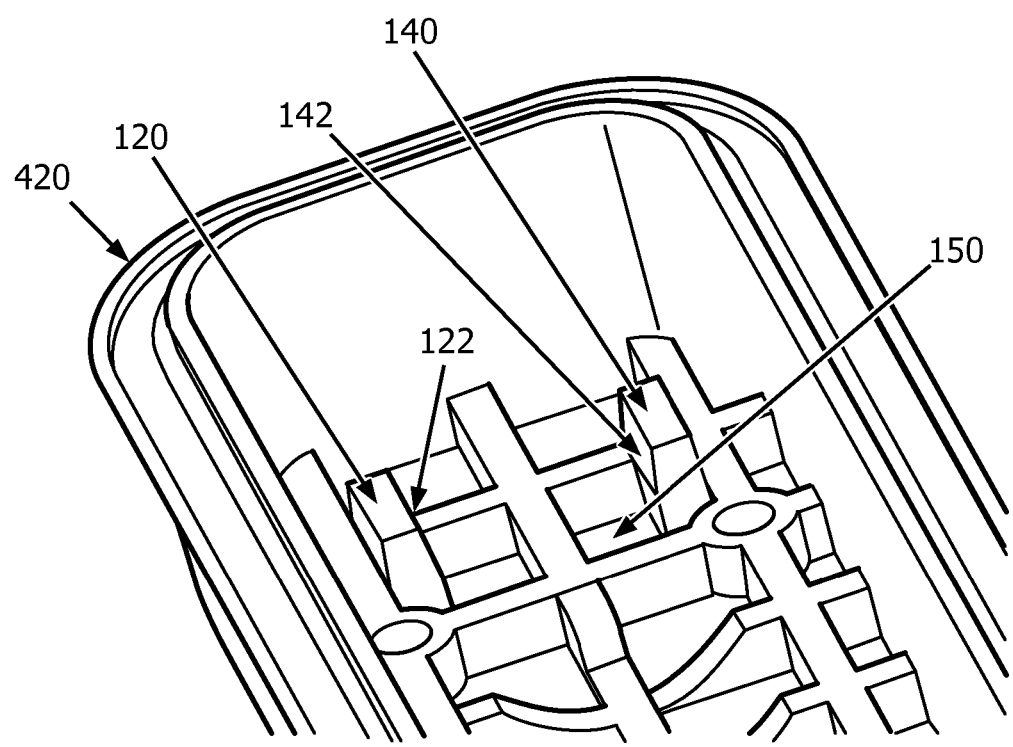
FIG. 8A is a diagrammatic perspective view of a back housing, according to aspects of the present disclosure.
Figure 8B:
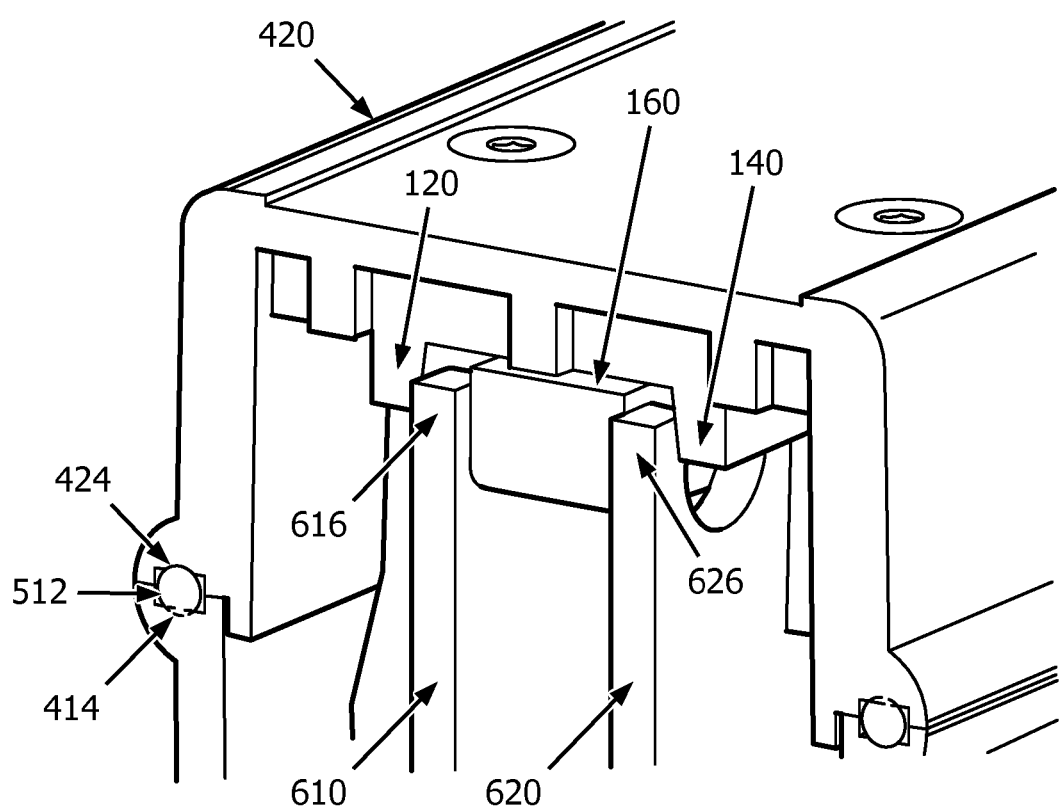
FIG. 8B is another diagrammatic perspective view of a back housing, according to aspects of the present disclosure.

FIGS. 8A and 8B diagrammatic perspective views of ribs 120 and 140 positioned on an inward-facing surface 150 of the back housing 420. Rib 120 includes a chamfer 122 and Rid 140 includes a chamfer 142. The angles of the chamfers 122, 142 can be between 1° and 60° in some instances, including values such as 15°, 20°, 30°, 45°, and/or other suitable values. As shown in FIG. 8A, in some embodiments, ribs 120 and 140 are positioned such that their chamfers 122 and 142 face one another, forming a space having a shrinking distance between chamfers 122 and 142 towards the inward-facing surface 150. As shown in FIG. 8B, in some instances, a portion 616 of the first PCB 610 and a portion 626 of the second PCB 620 are separated by a protrusion 160. When the connector assembly 400 is assembled, the portions 616 and 626, along with the protrusion 160 between them, are pushed towards the inward-facing surface 150 of the back housing 420, into the space between the chamfers 122 and 142. As the distance between chamfers 122 and 142 decreases towards the inward-facing surface 150, the first and second PCBs 610 and 620 are held in place between and strained by chamfers 122 and 142, on the one hand, and protrusion 160, on the other hand. In that regard, the chamfers 122 and 142 guide the portions 616 and 626 towards the inward-facing surface 150 and finally to a point where the portions 616 and 626 (with the protrusion 160 in between) could advance no further and are strained by the chamfers 122 and 142. In this respect, the chamfers 122 and 142 allow fast yet precise assembly of the connector assembly 400 and, in conjunction with the protrusion 160, and hold the first and second PCBs 610 and 620 in place.

Figure 9:
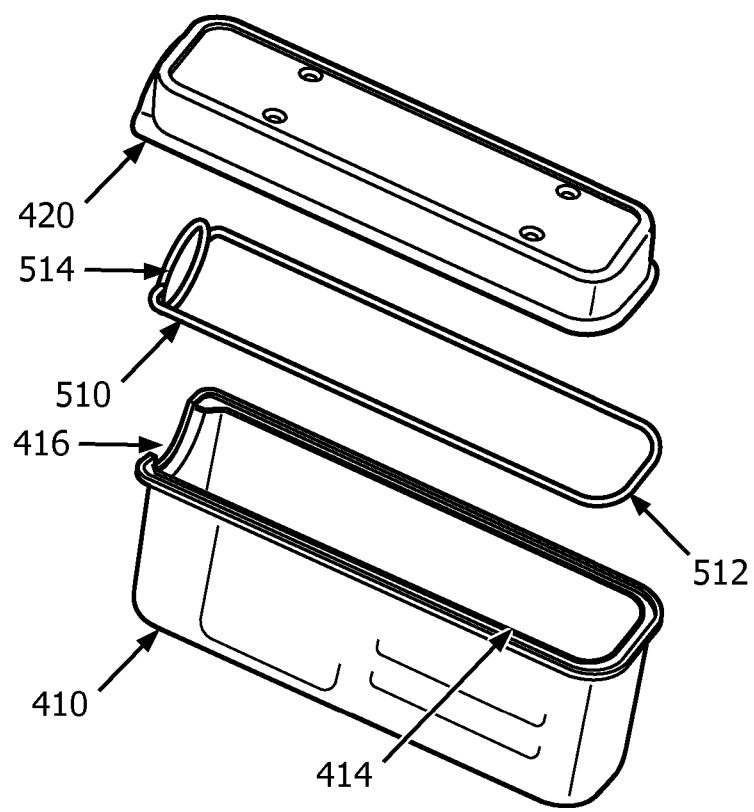
FIG. 9 is a diagrammatic perspective view of a front housing, a back housing, and a gasket, according to aspects of the present disclosure.
Figure 10:
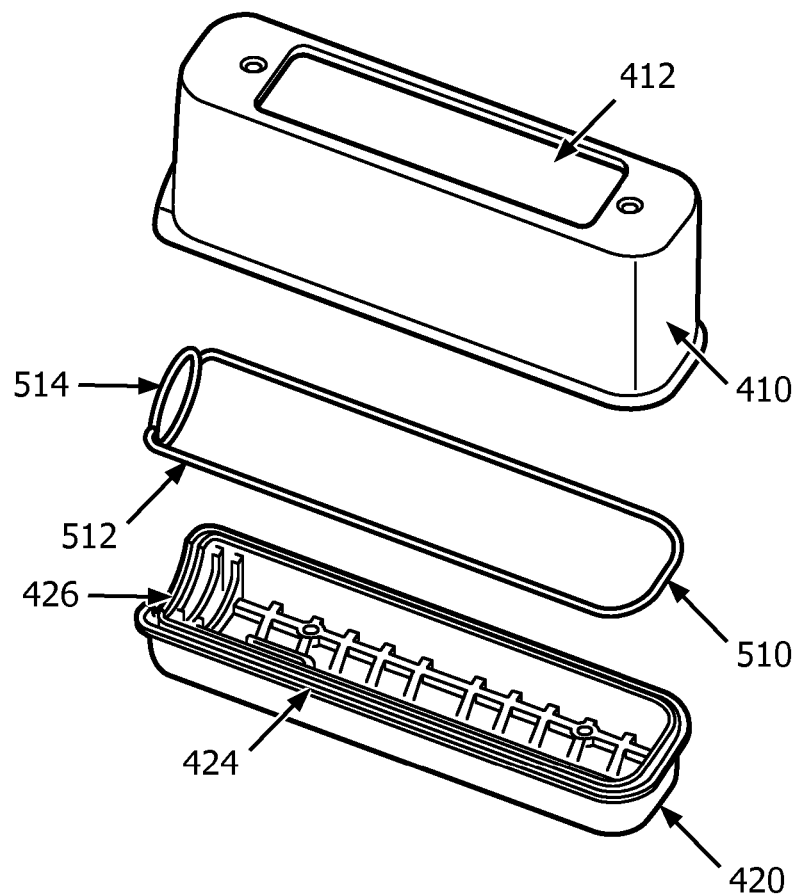
FIG. 10 is another diagrammatic perspective view of a front housing, a back housing, and a gasket, according to aspects of the present disclosure.

FIGS. 9 and 10 are diagrammatic perspective views of the front housing 410, the back housing 420, and the gasket 510, according to aspects of the present disclosure. FIG. 9 can be described as illustrating a downward facing view, while FIG. 10 illustrates an upward facing view of the same components of FIG. 9. In some embodiments, the front housing 410 and the back housing 420 are not directly coupled to one another. Rather, in such some embodiments, the front and back housings 410 and 420 can be coupled to one another when the front housing 410 is secured to the front internal frame 430 and the back housing 420 is secured to the back internal frame 440. The gasket 510 is disposed between the front housing 410 and the back housing 420. In some embodiments, the first 510 has a circular shaped member 514 and a rectangular shaped member 512. As shown in FIG. 9, the front housing 410 includes a groove 414 to receive the rectangular shaped member 512 of the gasket 510 and a semi-circular groove 416 to receive the circular shaped member 514 of the gasket 510. As shown in FIG. 10, the back housing 420 includes a groove 424 to receive the rectangular shaped member 512 of the gasket 510 and a semi-circular groove 426 to receive the circular shaped member 514 of the gasket 510. FIG. 8B shows how a rectangular shaped member 512 of the gasket 510 is received between the groove 414 of the front housing 410 and the groove 424 of the back housing 420.

As shown in FIGS. 3, 9, and 10, the front housing 410 and the back housing 420 are directly or indirectly coupled to one another along a plane parallel to the opening 412 for the connector 800. That is, the body connector assembly 400 is not split along a plane perpendicular to the opening 412. The arrangement of the connector assembly 400 illustrated in FIGS. 3, 9, and 10 advantageously eliminates a potential ingress point for fluid that would exist if the connector assembly 400 was split along the plane perpendicular to the opening 412. For example, in the arrangement of FIGS. 3, 9, and 10, the seam between housings 410, 420 is spaced from the opening 412, rather than being adjacent to the opening 412 if the connector assembly 400 was split along the plane perpendicular to the opening 412.

Figure 11A:
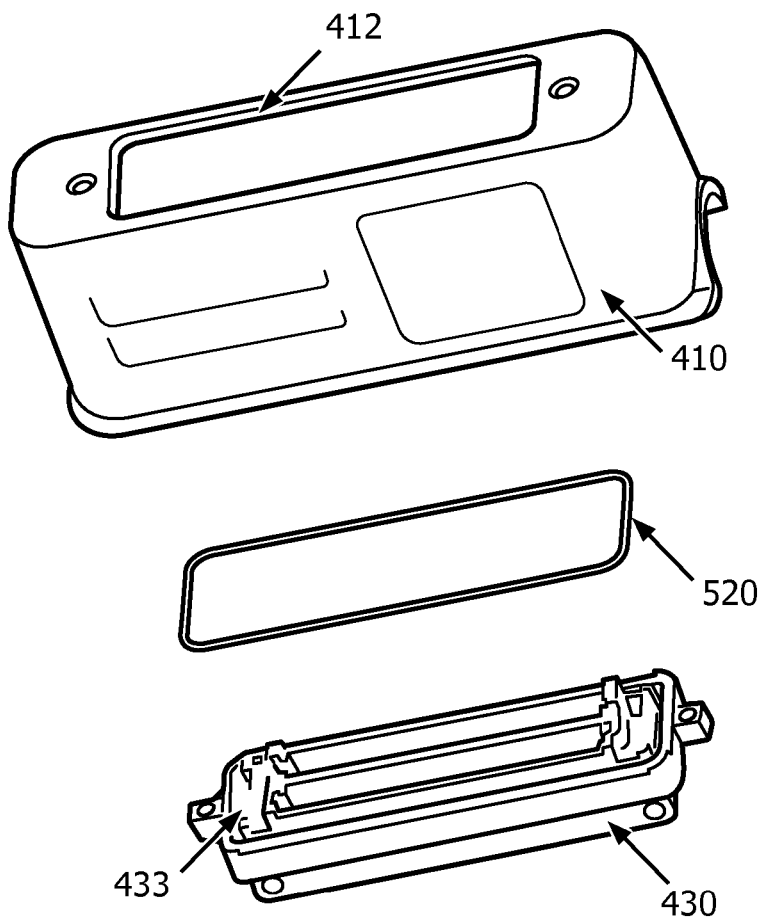
FIG. 11A is a diagrammatic perspective view of a front housing, a front internal frame, and a gasket, according to aspects of the present disclosure.
Figure 11B:
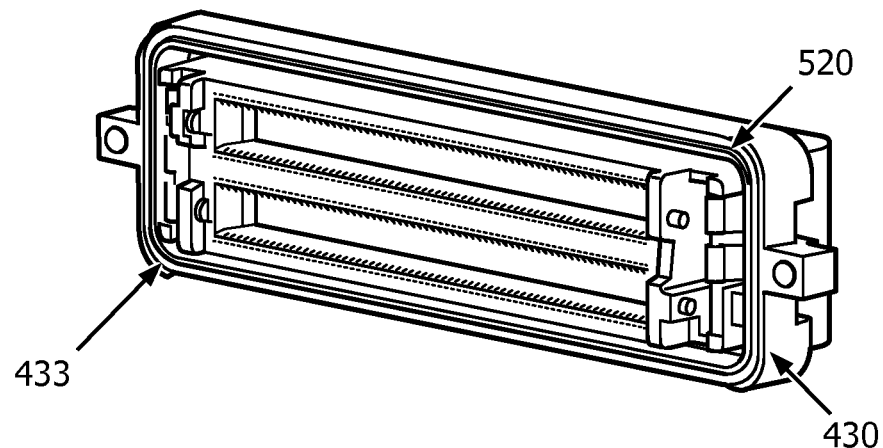
FIG. 11B is a diagrammatic perspective view of a front internal frame and a gasket, according to aspects of the present disclosure.

FIG. 11A is a diagrammatic perspective view of the front housing 410, the front internal frame 430, and the gasket 520, according to aspects of the present disclosure. In some embodiments, the front housing 410 is secured to the front internal frame 430. In some instances, the front housing 410 is secured to the front internal frame 430 by a plurality of screws. The second gasket 520 is coupled and/or otherwise disposed between an internal surface of the front housing 410 and the front internal frame 430. In some instances, the front internal frame 430 includes a groove 433 sized and shaped to receive a portion of the gasket 520. The second gasket 520 advantageously prevents fluid from entering the connector assembly 400 via the opening 412, when the connector assembly 400 is assembled with the connector 800 positioned within the front internal frame 430. In that regard, the gasket 520 seals the connector 800 and/or the front internal frame 430 against the inner surface of the front housing 410. FIG. 11B shows how a portion of the gasket 520 is received within the groove 433 of the front internal frame 430.

Figure 12:
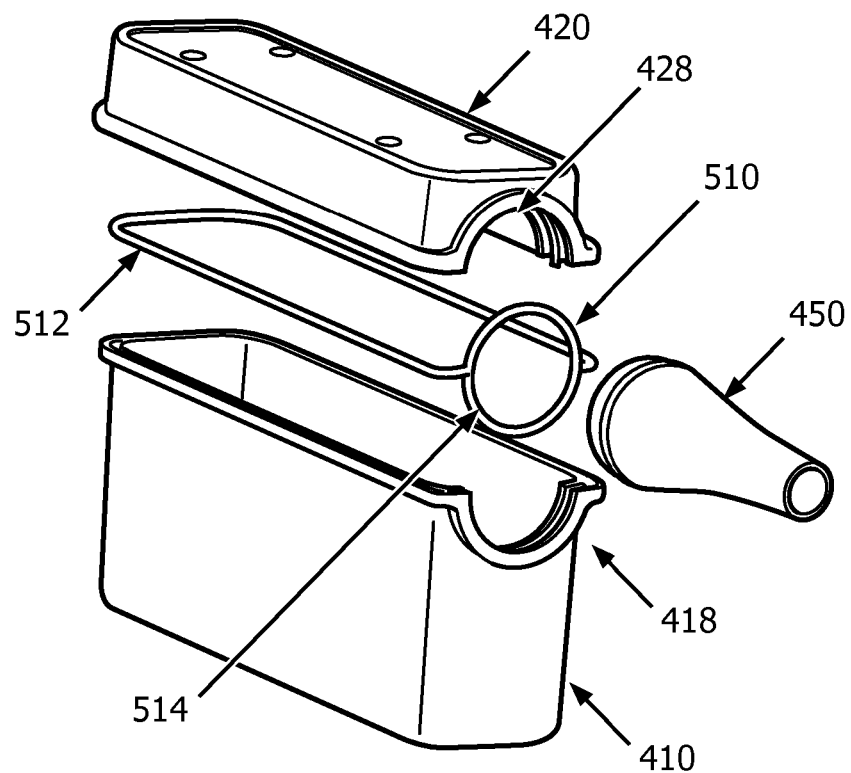
FIG. 12 is a diagrammatic perspective view of a front housing, a back housing, a gasket, and a conical cable housing, according to aspects of the present disclosure.

FIG. 12 is a diagrammatic perspective view of the front housing 410, the back housing 420, gasket 510, and the conical cable housing 450, according to aspects of the present disclosure. In some embodiments, the conical cable housing 450 is received between a semi-circular edge recess 418 of the front housing 410 and a semi-circular edge recess 428 of the back housing 420. In some embodiments, the circular shaped member 514 of gasket 510 is disposed between the conical cable housing 450 and the semi-circular edge recesses 418 and 428 of the first and back housing 410 and 420. The first gasket 510 advantageously prevents fluid ingress into the connector assembly 400 along the seams between the front housing 410, the back housing 420, and/or the conical cable housing 450. As also shown, the connector assembly can include a ridge that protrudes outward and is located at the split plane where the front housing 410 and the back housing 420 meet. This ridge provides a variety of functionality and ergonomic benefits, such as (1) increased protection of interior electrical components as the curvature of the ride helps wick moisture away from the split plane of the connector, (2) improved grip by the sonographer while inserting and removing from the system since after an Ultrasound exam, a sonographer will likely have gel over their gloves and the slippery gel makes it difficult to remove the connector without a firm feature to grip, and (3) improved grip while cleaning or transporting the probe as this will make the probe less likely to slip during handling and experience shock.

Figure 13:
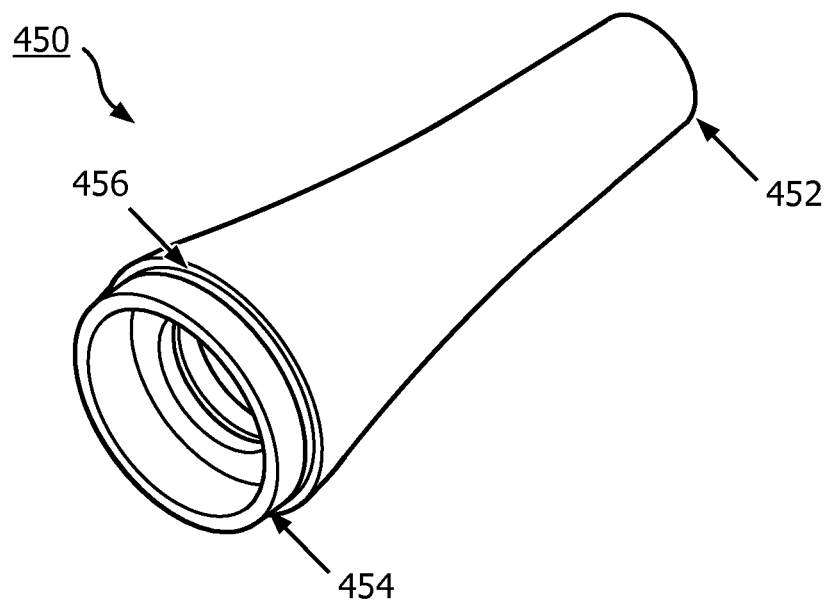
FIG. 13 is a diagrammatic perspective view of a conical cable housing, according to aspects of the present disclosure.

FIG. 13 is a diagrammatic perspective view of the conical cable housing 450, according to aspects of the present disclosure. In some embodiments, the conical cable housing 450 includes a proximal end 452 and a distal end 454. The proximal end 452 has a first diameter and the distal end 454 has a second diameter larger than the first diameter. As shown in FIG. 12, in come embodiments, the distal end 454 of the conical cable housing 450 is received between the semi-circular edge recesses 418 and 428 of the front and back housing 410 and 420. The distal end 454 of the conical cable housing 450 includes a circular groove 456 to receive a portion of the circular ring portion of the gasket 510.

Figure 14:
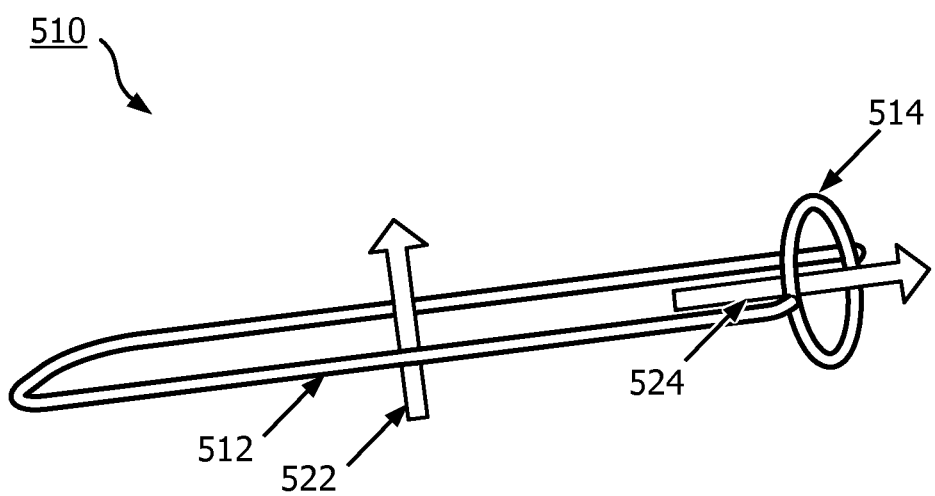
FIG. 14 is a diagrammatic perspective view of a gasket, according to aspects of the present disclosure.

FIG. 14 is a diagrammatic perspective view of the gasket 510, according to aspects of the present disclosure. In some embodiments, the gasket 510 includes a circular shaped member 514 and a rectangular shaped member 512. The rectangular shaped member 512 extends along a plane having a normal direction 522. The circular shaped member 514 extends along another plane having a normal direction 524. In some instances, the normal direction 522 is perpendicular to the normal direction 524.

Figure 15:
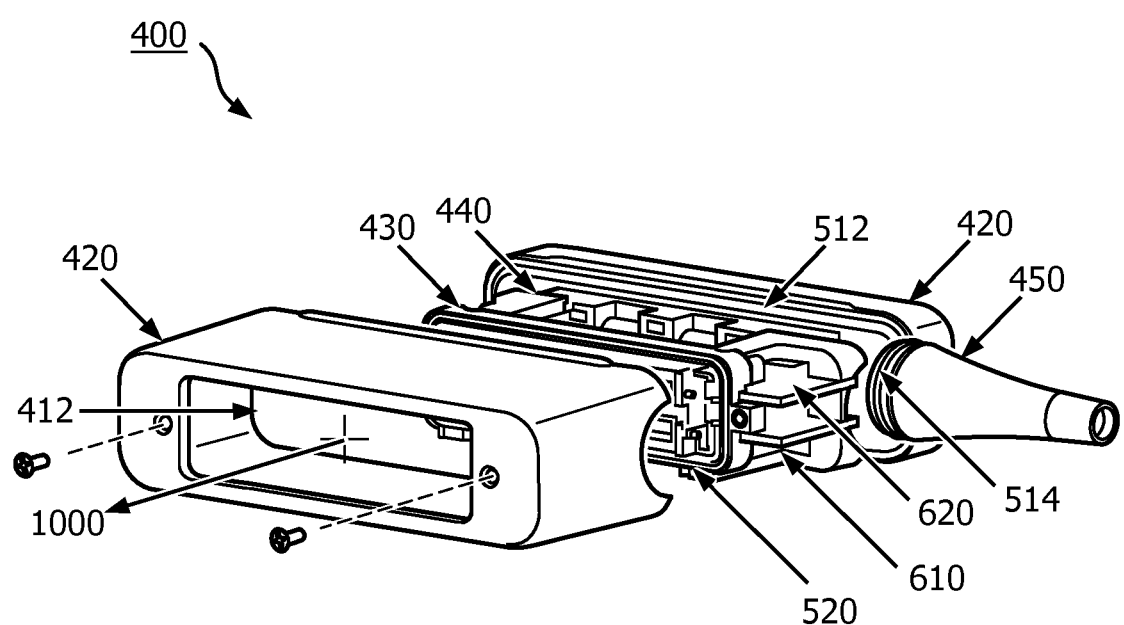
FIG. 15 is a diagrammatic partially exploded view of a connector assembly, according to aspects of the present disclosure.

Shown in FIG. 15 is a diagrammatic partially exploded view of the connector assembly 400, according to aspects of the present disclosure. In some embodiments, the opening 412 has a substantially rectangular shape along an opening plane and opens in an opening direction 1000 parallel to a normal direction of the opening plane. Both the rectangular shaped member 512 of the gasket 510 and the gasket 520 extend along planes having normal directions parallel to the opening direction 1000. In some embodiments, the front internal frame 430 and the back internal frame 440 are secured to one another, and the front and back housings 410 and 420 are secured to one another by being secured to the front and back internal frames 430 and 440. The circular shaped member 514 of the gasket 510 is disposed in the circular-shaped interface between the conical cable housing 450, on the one hand, and the front and back housings 410 and 420, on the other hand. The first and second gasket 510 and 520 serve as bather of humidity, disinfectants, ultrasound gel, bodily fluids, and enzymatic cleaners and protect the PCBs 610 and 620 from being damaged by ingress of the foregoing liquids. In this regard, structure of the connector assembly 400 advantageously allows for waterproofing while the connector assembly 400 is exposed to liquid (e.g., water, enzymatic cleaners, etc.) such during sterilization procedures in an autoclave, partial or full immersion, and/or other suitable procedures for cleaning and disinfection purposes.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A medical imaging device comprising:
   an imaging assembly at a distal portion of a flexible elongate member; and
   a connector assembly at a proximal portion of the flexible elongate member, wherein the connector assembly is configured to connect the medical imaging device to a terminal of a medical imaging system, the connector assembly comprising:
       a conical cable housing having a proximal end and a distal end, the proximal end having a first outer diameter, the distal end having a second outer diameter smaller than the first outer diameter;
       a front housing including:
           an opening sized and shaped to receive at least one electrical connector, and
           a semi-circular edge recess configured to receive a portion of a circumference of the proximal end of the conical cable housing;
       a back housing including a semi-circular edge recess configured to couple to a portion of the circumference of the proximal end of the conical cable housing;
       a front internal frame configured to be secured to the front housing;
       a back internal frame configured to be secured to the back housing; and
       at least one printed circuit board securely clamped along a planar direction thereof between the front internal frame and the back internal frame when the front internal frame is secured to the back internal frame.

2. The medical imaging device of claim 1, wherein the at least one printed circuit board comprises two printed circuit boards, wherein a portion of the two printed circuit boards are inserted into slots disposed in the back internal frame.

3. The medical imaging device of claim 1, wherein the at least one electrical connector is at least one female zero insertion force (ZIF) connector configured to be electrically connected to at least one male ZIF connector.

4. The medical imaging device of claim 1, wherein the back internal frame comprises a recess sized and shaped to receive a portion of a ferrite tube.

5. The medical imaging device of claim 4, wherein the back housing comprises a recess sized and shaped to receive a portion of the ferrite tube.

6. The medical imaging device of claim 1, wherein the connector assembly further comprises a gasket,
   wherein the front housing includes a first groove configured to receive a portion of the gasket, the first groove including a first curved groove positioned on the semi-circular edge recess,
   wherein the back housing includes a second groove configured to receive a portion of the gasket, the second groove including a second curved groove positioned on the semi-circular edge recess, and
   wherein when the front housing is secured to the front internal frame and the back housing is secured to the back internal frame, the gasket is disposed between the first groove and the second groove and between the first and second curved grooves and the circumference of the proximal end of the conical cable housing.

7. The medical imaging device of claim 6, wherein the circumference of the proximal end of the conical cable housing comprises a third groove configured to receive a portion of the gasket.

8. The medical imaging device of claim 6,
   wherein the gasket is a first gasket,
   wherein the connector assembly further comprises a second gasket and the front internal frame comprises a third groove configured to receive a portion of the second gasket, and
   wherein when the front housing is secured to the front internal frame, the second gasket is disposed between the front housing and the third groove.

9. The medical imaging device of claim 6, wherein the gasket includes a rectangular-shaped member extending along a first plane and a circular-shaped member extending along a second plane.

10. The medical imaging device of claim 9, wherein the first plane has a first normal direction and the second plane has a second normal direction, the first normal direction being perpendicular to the second normal direction.

11. A medical imaging device connector assembly for connecting a medical imaging device to a terminal of a medical imaging system, the medical imaging device connector assembly comprising:
    a conical cable housing having a proximal end and a distal end, the proximal end having a first outer diameter, the distal end having a second outer diameter smaller than the first outer diameter;
    a front housing including:
        an opening sized and shaped to receive at least one electrical connector, and
        a semi-circular edge recess configured to receive a portion of a circumference of the proximal end of the conical cable housing;

a back housing including a semi-circular edge recess configured to couple to a portion of the circumference of the proximal end of the conical cable housing;

a front internal frame configured to be secured to the front housing;

a back internal frame configured to be secured to the back housing; and at least one printed circuit board securely clamped along a planar direction thereof between the front internal frame and the back internal frame when the front internal frame is secured to the back internal frame.

12. The medical imaging device connector assembly of claim 11, wherein the at least one printed circuit board comprises two printed circuit boards, wherein a portion of the two printed circuit boards are inserted into slots disposed in the back internal frame.

13. The medical imaging device connector assembly of claim 11, wherein the at least one electrical connector is at least one female zero insertion force (ZIF) connector configured to be electrically connected to at least one male ZIF connector.

14. The medical imaging device connector assembly of claim 11, wherein the back internal frame comprises a recess sized and shaped to receive a portion of a ferrite tube.

15. The medical imaging device connector assembly of claim 14, wherein the back housing comprises a recess sized and shaped to receive a portion of the ferrite tube.

16. The medical imaging device connector assembly of claim 11, wherein the connector assembly further comprises a gasket, wherein the front housing includes a first groove configured to receive a portion of the gasket, the first groove including a first curved groove positioned on the semi-circular edge recess, wherein the back housing includes a second groove configured to receive a portion of the gasket, the second groove including a second curved groove positioned on the semi-circular edge recess, and wherein when the front housing is secured to the front internal frame and the back housing is secured to the back internal frame, the gasket is disposed between the first groove and the second groove and between the first and second curved grooves and the circumference of the proximal end of the conical cable housing.

17. The medical imaging device connector assembly of claim 16, wherein the circumference of the proximal end of the conical cable housing comprises a third groove configured to receive a portion of the gasket.

18. The medical imaging device connector assembly of claim 16, wherein the gasket is a first gasket, wherein the connector assembly further comprises a second gasket and the front internal frame comprises a third groove configured to receive a portion of the second gasket, and wherein when the front housing is secured to the front internal frame, the second gasket is disposed between the front housing and the third groove.

19. The medical imaging device connector assembly of claim 16, wherein the gasket includes a rectangular-shaped member extending along a first plane and a circular-shaped member extending along a second plane.

20. The medical imaging device connector assembly of claim 19, wherein the first plane has a first normal direction and the second plane has a second normal direction, the first normal direction being perpendicular to the second normal direction.

* * * * *